(12) United States Patent
Matsuura et al.

(10) Patent No.: US 10,526,272 B2
(45) Date of Patent: Jan. 7, 2020

(54) WATER ELIMINATION METHOD

(71) Applicant: DAIKIN INDUSTRIES, LTD., Osaka (JP)

(72) Inventors: Makoto Matsuura, Osaka (JP); Yosuke Kishikawa, Osaka (JP); Asako Yoshiyama, Osaka (JP); Sumi Ishihara, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/750,291

(22) PCT Filed: Aug. 5, 2016

(86) PCT No.: PCT/JP2016/073207
§ 371 (c)(1),
(2) Date: Feb. 5, 2018

(87) PCT Pub. No.: WO2017/026422
PCT Pub. Date: Feb. 16, 2017

(65) Prior Publication Data
US 2018/0222842 A1    Aug. 9, 2018

(30) Foreign Application Priority Data
Aug. 7, 2015 (JP) .................. 2015-157786

(51) Int. Cl.
| C07C 67/56 | (2006.01) |
| B01J 20/18 | (2006.01) |
| C07C 69/54 | (2006.01) |
| B01J 20/28 | (2006.01) |
| C07C 67/58 | (2006.01) |
| C07C 69/533 | (2006.01) |

(52) U.S. Cl.
CPC .............. *C07C 67/56* (2013.01); *B01J 20/18* (2013.01); *B01J 20/2808* (2013.01); *C07C 69/54* (2013.01); *C07C 67/58* (2013.01); *C07C 69/533* (2013.01)

(58) Field of Classification Search
CPC ....... B01J 20/18; B01J 20/2808; C07C 67/56; C07C 67/58; C07C 69/54; C07C 69/533
See application file for complete search history.

(56) References Cited

U.S. PATENT DOCUMENTS

| 2,882,243 A * | 4/1959 | Milton ............... B01J 20/18 208/2 |
| 5,364,553 A * | 11/1994 | Cao .................. C11D 1/29 510/321 |
| 6,179,966 B1 * | 1/2001 | Shimizu ................ C07C 51/46 159/47.1 |
| 8,242,308 B2 * | 8/2012 | Ho ..................... C07C 51/44 562/600 |
| 2012/0059187 A1 * | 3/2012 | Ishii ..................... C07C 67/317 560/213 |
| 2012/0283468 A1 | 11/2012 | Kreis et al. |
| 2015/0045579 A1 | 2/2015 | Li et al. |

FOREIGN PATENT DOCUMENTS

| DE | 102008043609 | 5/2010 |
| JP | 7-133252 | 5/1995 |
| JP | 2002-251009 | 9/2002 |
| JP | 2004-307586 | 11/2004 |
| JP | 2006-151923 | 6/2006 |
| JP | 2011-1340 | 1/2011 |
| JP | 2012-530756 | 12/2012 |

OTHER PUBLICATIONS

Acrylic acid, United Nations Environment Program International Labour Organisation World Health Organization, Environmental Health Criteria 191, IPCS ICHEM, 1997 49 pages (Year: 1997).*
International Search Report dated Oct. 25, 2016 in International (PCT) Application No. PCT/JP2016/073207.
The Chemical Society of Japan, fifth edition Jikken Kagaku Koza 26, Kobunshi Kagaku, Maruzen Co., Ltd., 2005, pp. 67-68, including english translation of Experimental Example 2 on p. 67.

(Continued)

*Primary Examiner* — Yate' K Cutliff
(74) *Attorney, Agent, or Firm* — Wenderoth, Lind & Ponack, L.L.P.

(57) ABSTRACT

An object of the present invention is to provide a method for efficiently eliminating water from a composition containing an acrylic acid derivative and water. This problem is solved by a method for eliminating water from a composition A containing:

(A) an acrylic acid derivative represented by Formula (I):

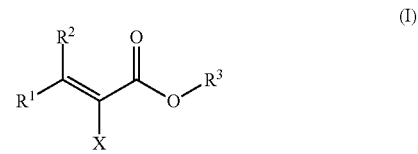

wherein $R^1$ and $R^2$ are identical or different, and each represents alkyl, fluoroalkyl, aryl that may have one or more substituents, halogen, or hydrogen, $R^3$ represents alkyl, fluoroalkyl, aryl that may have one or more substituents, or hydrogen, and X represents alkyl, fluoroalkyl, halogen, or hydrogen; and (B) water, the method comprising step A of bringing the composition A into contact with a zeolite.

6 Claims, No Drawings

(56) References Cited

OTHER PUBLICATIONS

Acrylic acid (EHC 191), IPCS INCHEM, IPCS [online], 1997, [retrieval date Oct. 12, 2016.], Internet:<URL:http://www.inchem.org/documents/ehc/ehc191.htm>, ISSN: 0250-863X.
Extended European Search Report dated Feb. 13, 2019 in corresponding European Application No. 16835119.5.

* cited by examiner

WATER ELIMINATION METHOD

TECHNICAL FIELD

The present invention relates to a method for eliminating water, in particular a method for eliminating water from a composition containing an acrylic acid derivative and water.

BACKGROUND ART

Acrylic acid derivatives are widely used for materials of water-absorbing polymers, materials of acrylic resins as a substitute for inorganic glass for use in window materials for buildings and vehicles, coverings for lighting equipment, lantern signs, road signs, daily necessities, office supplies, crafts, windscreens of watches, and the like, and acrylic resin coating materials. Fluorine-containing acrylic derivatives are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Examples of known methods for producing an acrylic acid derivative include a method of producing an acrylic acid derivative by oxidizing isobutylene or propylene, and a method of producing an acrylic acid derivative using ethylene, propyne, or the like as a starting material using a transition metal catalyst.

To produce a fluorine-containing acrylic acid derivative, Patent Document 1 discloses, for example, a method of reacting a 2-fluoropropionic ester with a nitrogen-bromine-bond-containing brominating agent in the presence of a radical initiator, and Patent Document 2 discloses a process for converting a 3-halo-2-fluoropropionic acid derivative to a substituted 2-fluoroacrylic acid derivative in the presence of at least one kind of base and at least one kind of polymerization inhibitor.

CITATION LIST

Patent Literature

Patent Document 1: JP2011-001340A
Patent Document 2: JP2012-530756A

SUMMARY OF INVENTION

Technical Problem

In the production of an acrylic acid derivative, water can undesirably coexist in a target acrylic acid derivative-containing composition.

Acrylic acid derivatives are hydrolyzed with water, which may possibly adversely affect the stability of the acrylic acid derivatives.

Therefore, more specifically, even a trace amount of water may possibly cause an adverse effect on desired reactions when an acrylic acid derivative is used, for example, in the applications mentioned above, i.e., synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Further, even a trace amount of water may also possibly cause an adverse effect on the preservability of acrylic acid derivatives.

Accordingly, the development of a method for efficiently eliminating water from a composition containing an acrylic acid derivative and water has been in demand.

An object of the present invention is to provide a method for efficiently eliminating water from a composition containing an acrylic acid derivative and water.

Solution to Problem

As a result of extensive research, the present inventors found that the following method can solve the above problems:

A method for eliminating water from composition A containing:
(A) an acrylic acid derivative represented by Formula (I):

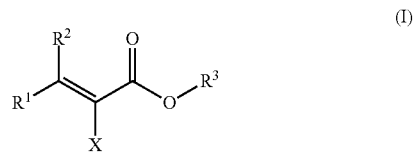

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen; and
(B) water,
the method comprising
step A of bringing composition A into contact with a zeolite.

The present invention has thus been accomplished.

The present invention encompasses the following embodiments.

Item 1. A method for eliminating water from a composition A containing:
(A) an acrylic acid derivative represented by Formula (I):

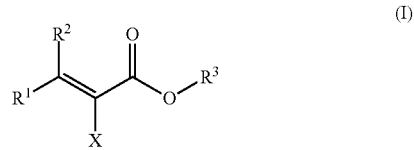

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen; and
(B) water,
the method comprising step A of bringing the composition A into contact with a zeolite.

Item 2. The method according to Item 1, wherein $R^1$ is hydrogen, $C_{1-20}$ alkyl, or $C_{1-20}$ fluoroalkyl.

Item 3. The method according to Item 1 or 2, wherein $R^2$ is hydrogen, $C_{1-20}$ alkyl, or $C_{1-20}$ fluoroalkyl.

Item 4. The method according to any one of Items 1 to 3, wherein $R^3$ is $C_{1-20}$ linear alkyl.

Item 5. The method according to any one of Items 1 to 4, wherein X represents $C_{1\text{-}20}$ alkyl, fluorine, chlorine, or hydrogen.

Item 6. The method according to any one of Items 1 to 5, wherein the zeolite is a synthetic zeolite.

Item 7. The method according to Item 6, wherein the zeolite is a synthetic zeolite having an average pore size of 3 to 5 Å.

Item 8. The method according to any one of Items 1 to 7, wherein the composition A is an organic phase obtained by washing with water a composition B containing the acrylic acid derivative represented by Formula (I) and a water-soluble impurity, and eliminating an aqueous phase generated by the washing.

Item 9. The method according to Item 8, wherein the water-soluble impurity is at least one member selected from the group consisting of alcohols and aldehydes.

Item 10. A composition containing: (A) an acrylic acid derivative represented by Formula (I):

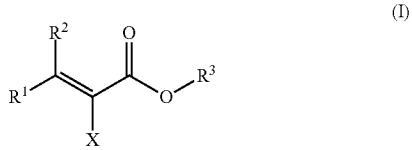

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen; and
(B) water,
wherein the water content in the composition is within a range of 1000 to 20000 ppm (w/w).

Item 11. A method for producing a composition containing (A) an acrylic acid derivative represented by Formula (I):

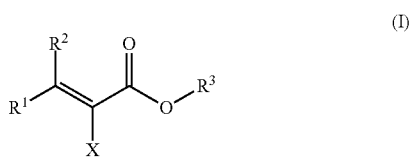

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen,
the method comprising any one of the methods of Items 1 to 9.

Item 12. A method for producing an acrylic acid derivative represented by Formula (I):

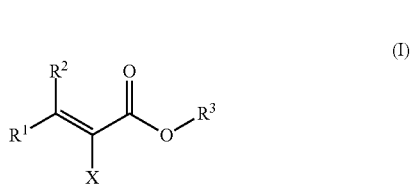

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen,
the method comprising any one of the methods of Items 1 to 9.

Advantageous Effects of Invention

An object of the present invention is to provide a method for efficiently eliminating water from a composition containing an acrylic acid derivative and water.

DESCRIPTION OF EMBODIMENTS

Terms

In this specification, "room temperature" refers to a temperature in a range of 10 to 40° C.

The symbols and the abbreviations in this specification are to be interpreted as having the general meanings in the related technical field to which the present invention pertains, according to the context of this specification, unless otherwise specified.

In this specification, the term "comprise/contain" encompasses the meanings of "consist essentially of" and "consist of."

In this specification, "alkyl" may be cyclic, linear, or branched.

In this specification, "alkyl" may be, for example, $C_{1\text{-}20}$, $C_{1\text{-}12}$, $C_{1\text{-}6}$, $C_{1\text{-}4}$, or $C_{1\text{-}3}$ alkyl.

In this specification, specific examples of "alkyl" include methyl, ethyl, propyl, isopropyl, butyl, isobutyl, sec-butyl, tert-butyl, pentyl, neopentyl, hexyl, and like linear or branched alkyl groups.

In this specification, specific examples of "alkyl" include cyclopropyl, cyclobutyl, cyclopentyl, cyclohexyl, and like $C_{3\text{-}6}$ cyclic alkyl (cycloalkyl).

In this specification, "fluoroalkyl" refers to alkyl in which at least one hydrogen is replaced by fluorine.

In this specification, the number of fluorine atoms in the "fluoroalkyl" may be one or more (e.g., 1 to 3, 1 to 6, 1 to 12, or 1 to the maximum replaceable number).

In this specification, examples of "fluoroalkyl" include $C_{1\text{-}20}$, $C_{1\text{-}12}$, $C_{1\text{-}6}$, $C_{1\text{-}4}$, and $C_{1\text{-}3}$ fluoroalkyl groups.

In this specification, "fluoroalkyl" may be linear or branched.

In this specification, specific examples of "fluoroalkyl" include fluoromethyl, difluoromethyl, trifluoromethyl, 2,2,2-trifluoroethyl, pentafluoroethyl, tetrafluoropropyl (e.g., $HCF_2CF_2CH_2$—), hexafluoropropyl (e.g., $(CF_3)_2CH$—), nonafluorobutyl, octafluoropentyl (e.g., $HCF_2CF_2CF_2CF_2CH_2$—), tridecafluorohexyl, and the like.

In this specification, examples of "aryl" include phenyl and naphthyl.

In this specification, examples of "halogen" include fluorine, chlorine, bromine, and iodine.

Water Elimination Method

The water elimination method of the present invention is a method for eliminating water from composition A containing: (A) an acrylic acid derivative (hereinafter may sometimes be referred to as "acrylic acid derivative (A)") represented by Formula (I):

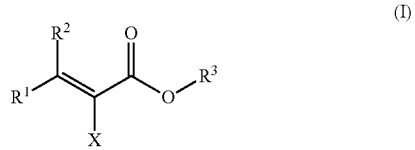

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen; and
(B) water,
the method comprising bringing composition A into contact with a zeolite.

Composition A to be subjected to the water elimination method of the present invention may be acrylic acid derivative (A) containing water as an impurity.

More specifically, one embodiment according to the present invention encompasses a method for purifying acrylic acid derivative (A), the method comprising bringing a roughly purified product of acrylic acid derivative (A) containing water as an impurity into contact with a zeolite to eliminate the water.

Acrylic acid derivative (A) may be a compound to be purified by a purification method comprising the method of the present invention.

In Formula (I), $R^1$ is preferably hydrogen, $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, or $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, and more preferably hydrogen.

In Formula (I), $R^2$ is preferably hydrogen, $C_{1-20}$ (preferably $C_{1-12}$ (preferably $C_{1-6}$, further preferably $C_{1-4}$, further more preferably $C_{1-3}$, particularly preferably $C_1$ or $C_2$) alkyl, or $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, and more preferably hydrogen.

In Formula (I), $R^3$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl, more preferably methyl or ethyl, and further more preferably methyl.

In Formula (I), X is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) alkyl, fluorine, chlorine, or hydrogen, more preferably methyl, fluorine, or hydrogen, and further more preferably fluorine.

In Formula (I), $R^3$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl, and X is preferably methyl or fluorine; and $R^3$ is more preferably methyl or ethyl (and further more preferably methyl), and X is methyl or fluorine.

In Formula (I), $R^1$ is preferably hydrogen, $R^2$ is preferably hydrogen, $R^3$ is preferably methyl or ethyl (and more preferably methyl), and X is preferably methyl, fluorine, or hydrogen (and more preferably fluorine).

Acrylic acid derivative (A) may be produced by a known method, or a method similar thereto. Alternatively, acrylic acid derivative (A) is commercially available.

Acrylic acid derivative (A) may be produced, for example, through the production method disclosed in WO 2014/034906, or a method similar thereto.

Composition A used in the method of the present invention is preferably a liquid.

In composition A used in the method of the present invention, acrylic acid derivative (A) is preferably mixed with water. That is, composition A used in the method of the present invention is preferably of a single phase in which a phase containing acrylic acid derivative (A) is not separated from a phase containing water.

The lower limit of the water content in composition A used in the method of the present invention is preferably 1000 ppm (w/w), more preferably 2000 ppm (w/w), and further more preferably 3000 ppm (w/w).

The upper limit of the water content in composition A used in the method of the present invention is preferably 20000 ppm (w/w), more preferably 15000 ppm (w/w), and further more preferably 10000 ppm (w/w).

The water content in composition A used in the method of the present invention is preferably within a range of 1000 to 20000 ppm (w/w), more preferably within a range of 2000 to 15000 ppm (w/w), and further more preferably within a range of 3000 to 10000 ppm (w/w).

The lower limit of the acrylic acid derivative (A) content in composition A used in the method of the present invention may be, but is not limited to, for example, 85% (w/w), 90% (w/w), or 95% (w/w).

The upper limit of the acrylic acid derivative (A) content in composition A used in the method of the present invention may be, but is not limited to, for example, 90% (w/w), 95% (w/w), or 99% (w/w).

The lower limit of the amount ratio of water/acrylic acid derivative (A) in composition A used in the method of the present invention is preferably 1000 ppm (w/w), more preferably 1050 ppm (w/w), and further more preferably 1100 ppm (w/w).

The upper limit of the amount ratio of water/acrylic acid derivative (A) in composition A used in the method of the present invention is preferably 25000 ppm (w/w), more preferably 18000 ppm (w/w), and further more preferably 11000 ppm (w/w).

The amount ratio of water/acrylic acid derivative (A) in composition A used in the method of the present invention is preferably within a range of 1000 to 25000 ppm (w/w), more preferably within a range of 1050 to 18000 ppm (w/w), and further more preferably within a range of 1100 to 11000 ppm (w/w).

Composition A used in the method of the present invention may contain one or more other substances, in addition to acrylic acid derivative (A) and water.

The zeolite used in the method of the present invention may be a natural zeolite or a synthetic zeolite.

The zeolite used in the method of the present invention is preferably, for example, a synthetic zeolite.

The zeolite used in the method of the present invention is preferably represented by a general formula:

$M_{2/n}O\cdot Al_2O_3\cdot xSiO_2\cdot yH_2O$ (M represents a metal cation, n represents its atomic valence, x represents a coefficient, and y represents a coefficient). M is preferably at least one metal cation selected from the group consisting of sodium cation and potassium cation.

The zeolite used in the method of the present invention is preferably represented by chemical formula:

$Na_{12}[(AlO_2)_{12}(SiO_2)_{12}]\cdot 27H_2O$.

The zeolite used is the method of the present invention is preferably porous.

The zeolite used is the method of the present invention preferably has an average pore size of 3 to 5 Å (preferably 3 to 4 Å).

Such zeolite is commercially available. Specific examples include molecular sieves 3A, 4A, and 5A (Union Showa K.K.), Zeolum 3A and 4A (Tosoh Corporation), and the like.

The zeolite used in the method of the present invention is preferably, for example, molecular sieve 3A or molecular sieve 4A, and more preferably, for example, molecular sieve 4A.

The zeolite used in the method of the present invention may be in the form of, for example, powder, granule, or pellets, and preferably powder or granule.

The zeolite used in the method of the present invention preferably has a weight average particle size of 10 μm or less, and more preferably 5 μm or less. The particle size as used herein refers to the major axis. In this specification, when zeolite primary particles constitute secondary particles, the term "weight average particle size" refers to the particle size of the secondary particles.

In the method of the present invention, the zeolite may be of a single kind, or a combination of two or more kinds.

The zeolite used in the method of the present invention may be subjected to activation treatment before use.

The conditions for the activation treatment may be, for example, a dry treatment in which heating is performed overnight at a temperature within a range of 300 to 350° C. in vacuum ($10^{-1}$ to $10^{-3}$ mmHg).

In the method of the present invention, a zeolite that has not been subjected to such an activation treatment can also be suitably used.

The amount of zeolite used in the method of the present invention is preferably, for example, within a range of 0.1 to 50 parts by mass, more preferably 0.3 to 40 parts by mass, and further more preferably within a range of 0.5 to 30 parts by mass, per 100 parts by mass of the water contained in composition A.

In the method of the present invention, the method for bringing composition A into contact with a zeolite is not particularly limited as long as composition A comes into contact with the zeolite. This method may be performed batchwisely, or continuously. Examples of batchwise methods include a method comprising placing a zeolite into a container containing composition A, optionally stirring the mixture, and after a defined period of time, eliminating the zeolite by filtration or the like. Examples of the continuous methods include a method comprising allowing compound A to pass through a zeolite-containing column.

In the method of the present invention, the temperature at which composition A is brought into contact with a zeolite is, for example, within a range of −10 to 50° C. or within a range of 0 to 40° C.

In the method of the present invention, the temperature at which composition A is brought into contact with a zeolite may be room temperature.

In the method of the present invention, the time for composition A to be in contact with a zeolite is appropriately set so as to be sufficient to enable desirable elimination of water. Specifically, for example, in a batchwise method, the times is usually 1 minute or more, and, for example, within a range of 0.1 to 5 hours or within a range of 0.3 to 2.5 hours.

Composition A used in the method of the present invention may be, for example, an organic phase obtained by washing with water composition B containing:
(A) an acrylic acid derivative represented by Formula (I):

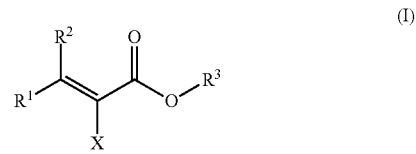

(I)

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents alkyl, fluoroalkyl, halogen, or hydrogen; and a water-soluble impurity, and
eliminating the aqueous phase generated by the washing.

The "water-soluble impurity" as used herein may be a substance that has solubility in water to a degree such that the impurity can be eliminated by water-washing under common conditions.

Examples of such a water-soluble impurity include alcohols, such as methanol, ethanol, and propanol; aldehydes, such as formaldehyde; and the like. These impurities may be used alone, or in a combination of two or more.

The total amount of the water-soluble impurity contained in composition A that is an organic phase obtained by water-washing above, is preferably 3% (w/w) or less, and more preferably 1% (w/w) or less.

The upper limit of water content in composition A from which all or some of the water was eliminated by using the method of the present invention (this composition may sometimes be referred to as "composition A'") may be, for example, 2000 ppm (w/w), 1800 ppm (w/w), 1600 ppm (w/w), 1400 ppm (w/w), 1200 ppm (w/w), 1000 ppm (w/w), or 800 ppm (w/w).

The lower limit of the water content in composition A' may be, for example, 100 ppm (w/w), 200 ppm (w/w), 300 ppm, 400 ppm (w/w), 500 ppm (w/w), or 600 ppm (w/w).

In one embodiment according to the present invention, the numerical value of the water content can serve as the amount ratio of water/composition A'.

In one embodiment according to the present invention, the numerical value of the water content can serve as the amount ratio of water/acrylic acid derivative (A).

EXAMPLES

The present invention is described below in more detail with reference to Examples. However, the present invention is not limited to these Examples.

The following are the meanings of the symbols and abbreviations used in the Examples. In addition, symbols and abbreviations usually used in the related technical field to which the present invention pertains may be used in this specification.

In the following Examples, the water content was measured by a Karl Fischer moisture meter.

In the following Examples, the amount of methanol was measured by gas chromatography.

In the following Examples, the amounts of methyl methacrylate and 2-fluoroacrylic acid methyl ester were measured by gas chromatography.

Example A

Example A1

A sample of methyl methacrylate containing 5100 ppm (w/w) of water was prepared. Then, 5 wt % of a molecular sieve (MS4A (powder), Union Showa K.K.) was added to the sample, followed by stirring for 0.5 h. The water content in the sample after stirring was 1350 ppm (w/w) (i.e., the water elimination rate was 73.5%).

Example B

Water-Washing (Elimination of Methanol from Methanol-Containing Sample (Preparation of Water-Containing Sample))

A sample in which the amount ratio of methanol/2-fluoroacrylic acid methyl ester was 41.5% (w/w) was prepared (sample before water-washing).

The sample (sample before water-washing) was washed with 2.0-fold mass of water.

The methanol content in the sample after water-washing as the amount ratio of methanol/2-fluoroacrylic acid methyl ester was 0.53% (w/w).

The recovery of 2-fluoroacrylic acid methyl ester was 67.8%.

The water content in the sample after water-washing was 4900 ppm (w/w).

Comparative Example B1, Comparative Example B2, Example B1, and Example B2 (Elimination of Water)

Samples of 2-fluoroacrylic acid methyl ester containing water in the amounts shown in Table 1 were prepared by using a method similar to the water-washing above. As shown in Table 1, the samples had different water contents. The difference is within the possible range among different preparation lots. The methanol content in each sample as the amount ratio of methanol/2-fluoroacrylic acid methyl ester was 0.53% (w/w).

$MgSO_4$ as a dehydrating agent and molecular sieve 4A (MS-4A (powder), Union Showa K.K.) or molecular sieve 3A (MS-3A (powder), Union Showa K.K.) were added at an amount ratio of 5% (w/w) to each sample, and the mixtures were gently stirred for 5 or 2 hours. Thereafter, the samples from which the dehydrating agent was eliminated were obtained by filtration, followed by measurement of water contents and calculation of water reduction rates. Table 1 shows the results.

TABLE 1

|  | Dehydrating agent | Amount of dehydrating agent added (% (w/w)) | Time (hr) | Water content before drying (ppm (w/w)) | Water content after drying (ppm (w/w)) | Water elimination rate (%) |
|---|---|---|---|---|---|---|
| Comp. Ex. B1 | $MgSO_4$ | 5 | 0.5 | 17010 | 5897 | 65.3 |
| Comp. Ex. B2 | $MgSO_4$ | 5 | 2 | 15894 | 5567 | 65.0 |
| Comp. Ex. B3 | $MgSO_4$ | 5 | 1 | 4384 | 3407 | 22.3 |
| Example B1 | MS-4A | 5 | 0.5 | 4900 | 659 | 86.5 |
| Example B2 | MS-3A | 5 | 2 | 7399 | 1699 | 77.0 |

The results shown in Table 1 clearly indicate that the use of a molecular sieve enabled efficient water elimination from a roughly purified product of 2-fluoroacrylic acid methyl ester containing water. However, the use of $MgSO_4$, which is widely used as an excellent dehydrating agent, could not efficiently eliminate water, although it showed an effect to some extent.

The invention claimed is:

1. A method for eliminating water from a composition A containing:

(A) an acrylic acid derivative represented by Formula (I):

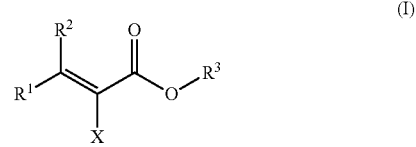

(I)

wherein
$R^1$ and $R^2$ are identical or different, and each represents alkyl, fluoroalkyl, aryl that may have one or more substituents, halogen, or hydrogen,
$R^3$ represents $C_{1-20}$ linear alkyl, and
X represents fluorine; and (B) water,
the method comprising step A of bringing the composition A into contact with a zeolite,
wherein the composition A is an organic phase obtained by washing with water a composition B containing the acrylic acid derivative represented by Formula (I) and a water-soluble impurity, and eliminating an aqueous phase generated by the washing, and
wherein the water-soluble impurity is at least one member selected from the group consisting of alcohols and aldehydes.

2. The method according to claim 1, wherein $R^1$ is hydrogen, $C_{1-20}$ alkyl, or $C_{1-20}$ fluoroalkyl.

3. The method according to claim 1, wherein $R^2$ is hydrogen, $C_{1-20}$ alkyl, or $C_{1-20}$ fluoroalkyl.

4. The method according to claim 1, wherein the zeolite is a synthetic zeolite.

5. The method according to claim 4, wherein the zeolite is a synthetic zeolite having an average pore size of 3 to 5 Å.

6. A composition containing:
(A) an acrylic acid derivative represented by Formula (I):

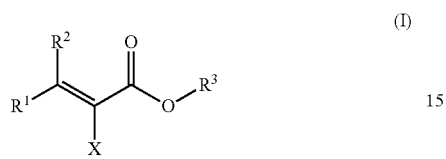

wherein
$R^1$ and $R^2$ are identical or different, and each represents alkyl, fluoroalkyl, aryl that may have one or more substituents, halogen, or hydrogen,
$R^3$ represents alkyl, fluoroalkyl, aryl that may have one or more substituents, or hydrogen, and
X represents fluorine; and
(B) water,
wherein the water content in the composition is within a range of 100 to 1400 ppm (w/w).

* * * * *